United States Patent [19]

Watson et al.

[11] Patent Number: 5,137,529
[45] Date of Patent: Aug. 11, 1992

[54] INJECTION PORT

[75] Inventors: David A. Watson, Goleta; Mark J. Licata, Santa Barbara; Alfons Heindl, Goleta; Edward C. Leicht, Goleta, all of Calif.

[73] Assignee: Pudenz-Schulte Medical Research Corporation, Goleta, Calif.

[21] Appl. No.: 679,658

[22] Filed: Apr. 2, 1991

Related U.S. Application Data

[63] Continuation-in-part of Ser. No. 483,089, Feb. 20, 1990, abandoned.

[51] Int. Cl.⁵ .......................... A61K 9/22; A61M 5/32
[52] U.S. Cl. ................................ 604/891.1; 604/175; 604/8; 128/DIG. 12
[58] Field of Search ......................... 604/86, 88, 49, 93, 604/175, 185, 123, 124, 126, 891.1, 8–10; 128/DIG. 12

[56] References Cited

U.S. PATENT DOCUMENTS

| | | |
|---|---|---|
| 3,951,147 | 4/1976 | Tucker et al. |
| 4,133,441 | 1/1979 | Mittleman et al. |
| 4,496,343 | 1/1985 | Prosl et al. |
| 4,543,088 | 9/1985 | Bootman et al. |
| 4,557,722 | 12/1985 | Harris |
| 4,559,033 | 12/1985 | Stephen et al. |
| 4,573,994 | 3/1986 | Fischell et al. ................... 604/891.1 |
| 4,634,424 | 1/1987 | O'Boyle |
| 4,634,427 | 1/1987 | Hannula et al. |
| 4,655,765 | 4/1987 | Swift ................................ 604/891.1 |
| 4,673,394 | 6/1987 | Fenton, Jr. et al. |
| 4,681,560 | 7/1987 | Schulte et al. |
| 4,685,905 | 8/1987 | Jeanneret |
| 4,704,103 | 11/1987 | Stober et al. |
| 4,718,894 | 1/1988 | Lazorthes |
| 4,762,517 | 8/1988 | McIntyre et al. |
| 4,767,410 | 8/1988 | Moden et al. |
| 4,772,270 | 9/1988 | Wiita et al. |
| 4,781,680 | 11/1988 | Redmond et al. |
| 4,784,646 | 11/1988 | Feingold ............................. 604/175 |
| 4,904,241 | 2/1990 | Bark ....................................... 604/93 |
| 5,085,644 | 2/1992 | Watson et al. ...................... 604/153 |

FOREIGN PATENT DOCUMENTS 2131496  6/1984  United Kingdom ............. 604/891.1

*Primary Examiner*—John D. Yasko
*Assistant Examiner*—Adam J. Cermak
*Attorney, Agent, or Firm*—Kelly, Bauersfeld & Lowry

[57] ABSTRACT

A subcutaneously implantable injection port includes an elastomeric outer housing which encloses an easily assemblage multi-piece rigid base structure. An injection chamber is defined between an upper septum, formed integrally with the elastomeric outer housing, and the underlying base structure. The outer housing includes an upper dome and a lower reinforced sheet. The septum, which is formed integrally with the upper dome, includes a septum flange which is compressed, interiorly of the outer housing, between two base members. A filter extends across the injection chamber dividing it into upper and lower portions. A needle guard, provided by one of the base components, prevents contact between a needle inserted into the injection chamber and the filter. An outlet connector integrally formed with one of the base components extends through the outer housing for connecting a catheter or the like, with the lower portion of the injection chamber. In assembling the injection port, a first base member or rigid outer ring is placed adjacent to an interior surface of the elastomeric outer housing. A filter is placed within a second base member and held securely in place thereon by a third base member which provides the needle guard and fits within the second base member in an interference fit. This assembly is pushed into the first base member in a manner compressing the septum flange and creating a fluid-tight injection chamber.

17 Claims, 2 Drawing Sheets

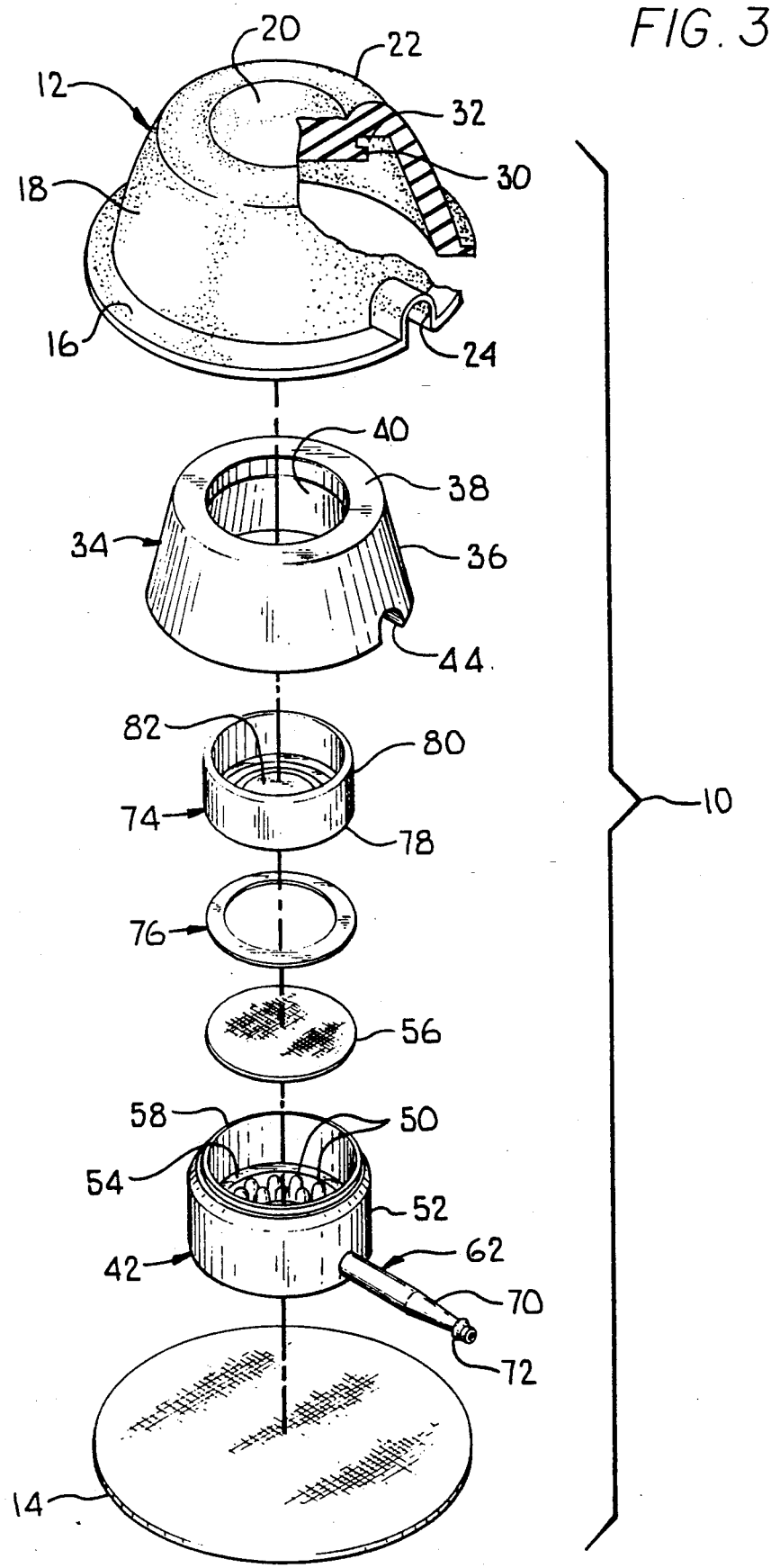

INJECTION PORT

RELATED APPLICATION

This is a continuation-in-part application of U.S. patent application Ser. No. 07/483,089, filed Feb. 20, 1990 and entitled SUBCUTANEOUS INJECTION PORT, now abandoned.

BACKGROUND OF THE INVENTION

This invention relates generally to medical devices which are implantable in the human body. More particularly, the present invention relates to a subcutaneously implantable direct delivery access port for repeated intermittent injection, which may be used in connection with a subcutaneous drug infusion apparatus.

Some medical treatments, such as chemotherapy, require repeated introduction of chemical substances into a patient's body. Often these chemical substances are introduced into a specific body site. Earlier, it was typical for such chemicals to be introduced by intravenous injection through the patient's skin into a vein. Such repeated venipuncture injections are painful and often difficult, especially with elderly patients. Additionally, some drugs are highly reactive and so traumatic to small peripheral veins that the veins cannot tolerate multiple injections. Also, such intravenous injections are often undesirable because the need for controlled long term introduction cannot be attained.

In order to overcome some of the drawbacks associated with repeated venipuncture injections, implantable infusate injection ports have been developed which typically include an internal chamber, a penetrable self-sealing septum, and a hollow male outlet connector, all of which are implanted subcutaneously within the patient. Such injection ports provide a permanent injection site without immobilizing the patient.

Normally a device of this type is surgically implanted in a patient so that it is positioned beneath the skin with the septum facing outwardly. Often the outlet connector is attached to a catheter element for transmitting fluids to a predetermined area of the patient's body, such as a large vein. Once an injection port of this type has been installed in a patient, the internal chamber can be periodically filled with medication by inserting a hypodermic needle in the patient so that it penetrates the skin and passes through the septum for injecting medication into the internal chamber. It has been found that injection ports of this general type can be effectively utilized for dispensing medication in the body of a patient over a prolonged period of time, and that it is generally preferable to a catheter or the like which would require a permanent opening in the skin.

Subcutaneous injection ports can also be used for the administration of medication to a patient. For example, in many therapeutic procedures there is a need to implant a drug delivery device. Such an implantable drug delivery device provides a bolus or therapeutic dose of the drug contained therein to a particular location within the patient's body. In order to replenish the drug in the implanted device, a self-sealing subcutaneous injection port can be provided in fluid communication with the drug delivery device. An exemplary drug delivery device is shown in U.S. Pat. No. 4,681,560, the contents of which are incorporated herein by reference. The subcutaneous injection port provides a means for administering additional medicament into the device as the medicament can be injected using a syringe inserted subcutaneously into the injection port without the need for a subsequent surgical procedure.

Depending on the drug delivery device, it may be extremely important, and even critical in some instances, that small foreign substances introduced into the injection port be kept from passing to the delivery device and, ultimately, to the patient. Particulate foreign substances may be inadvertently "picked-up" as the needle is pushed through a patient's skin just prior to insertion into the injection port. Filters have been utilized to screen out undesirable small particulate foreign matter prior to the injected fluid being allowed to exit the injection port.

In using subcutaneous injection ports for the injection of drugs, great care must be taken to insure that the hypodermic needle punctures the septum and is not deflected away by the supporting structure so that the drug is accidentally introduced into the subcutaneous pocket within which the device is located. As mentioned above, with certain drugs this type of extravasation can be extremely serious. Moreover, certain prior art devices tend to leak around the puncture site, or around the internal reservoir of the device, particularly under conditions of back pressure experienced during the injection step.

Accordingly, there has been a need for an improved subcutaneous injection port of simplified construction and having an assembly process which virtually eliminates any possibility of leakage from the internal chamber. Additionally there exists a need for such an improved injection port which presents a unitized elastomeric exterior, wherein the septum is integrally formed with the body of the port. This again would tend to minimize fluid leakage. Further, such an injection port is needed which provides adequate compression of the septum about its periphery between at least two rigid members. Preferably these rigid members would not have surfaces exposed exteriorly of the injection port, with the possible exception of an outlet connector. The assembly process should preferably maximize use of interference fittings between components, and minimize any requirement for the use of adhesive sealants or other time consuming manufacturing steps. The present invention fulfills these needs and provides other related advantages.

SUMMARY OF THE INVENTION

The present invention resides in an improved subcutaneous injection port and in a novel assembly process which permits the injection port to be quickly and easily assembled in a manner which virtually eliminates the possibility of unintended fluid leakage therefrom. The injection port comprises, generally, an elastomeric outer housing including an integral elastomeric septum, at least two base components situated within the outer housing which compress a portion of the septum therebetween, a filter barrier, and an outlet. The outlet extends from a lower portion of a internal injection chamber exteriorly through the outer housing.

In a preferred form of the invention, the elastomeric outer housing includes an upper dome attached to a lower reinforced sheet. The upper dome includes a lower flange, a frusto-conical side wall extending upwardly from the lower flange, and a septum integrally formed with the side wall and supported thereby in spaced relation to the lower reinforced sheet. The septum includes a peripheral flange which extends circumferentially outwardly from the body of the septum toward the side wall.

A rigid first base member is enclosed within the elastomeric outer housing and comprises a generally frustoconical ring which is configured to contiguously engage and support an interior surface of the side wall. The first base member includes a rigid upper flange which overlies the septum peripheral flange and provides a rigid barrier between the peripheral flange of the septum and the adjacent side wall portions.

A rigid second base member is situated within the first base member and the elastomeric outer housing. The second base member is cup-shaped and includes a floor and a continuous wall extending upwardly therefrom. The continuous wall engages an inner surface of the first base member in an interference fit. The floor has upwardly extending filter supports for supporting the filter barrier. These upwardly extending supports form a labyrinth passageway in open fluid communication with the outlet. The second base member defines, together with the septum, an internal injection chamber. The upper edge of the continuous wall forms an upper septum-engaging section which compresses the septum peripheral flange against the upper flange of the first base member. Notably, the compression of the septum occurs entirely within the elastomeric outer housing. Thus the possibility of leakage occurring due to seepage between the septum and the base member is eliminated.

The filter barrier is supported directly over the upwardly extending supports of the second base member to separate the injection chamber into an upper portion adjacent to the septum, and a lower portion. The filter barrier comprises a two-tenths micron filter. Means are provided for sealing an outer peripheral flange of the filter barrier adjacent to the second base member, to require any fluid injected into the upper portion of the injection chamber to pass through the filter barrier before exiting the injection port.

The sealing means include a needle guard for preventing contact between a needle inserted through the septum into the injection chamber, and the filter barrier. In particular, the sealing means comprise a third rigid base member which is cup-shaped and includes a filter barrier-engaging base, a continuous wall which extends upwardly therefrom, and a floor spaced from the filter barrier and supported by the base. The continuous wall of the third base member engages an inner surface of the second base member in an interference fit, and includes an upper septum-engaging section which underlies the septum peripheral flange and compresses the septum peripheral flange against the upper flange of the first base member. Further, a gasket is disposed between the third base member and the outer peripheral flange of the filter barrier.

The outlet extends from the lower portion of the injection chamber exteriorly through the housing. The outlet includes a rigid outlet connector formed integrally with the second base member to provide a fluid conduit from an inlet port on an interior surface of the second base member, to an outlet port situated at an opposite end of the outlet connector. The outlet connector may be inserted within a catheters or standard surgical tubing, to connect the injection port with a desired portion of a body or to a drug delivery device. A radiopaque seal tube encircles a portion of the outlet connector.

As noted above, the present invention also resides in a novel process for manufacturing a subcutaneously implantable injection port. The manufacturing process generally comprises the steps of: providing an elastomeric outer housing including an integral elastomeric septum; placing a first base member entirely within the outer housing such that a rigid upper flange of the first base member contiguously engages a peripheral flange of the septum, wherein the first base member has a generally cylindrical inner surface; and inserting a second base member entirely within the first base member to compress the septum peripheral flange between the first and second base members and to form an internal injection chamber between the septum and the second base member. The second base member has a generally cylindrical outer surface configured to engage the generally cylindrical inner surface of the first base member in a fluid-tight interference fit.

More specifically with respect to a preferred form of the manufacturing process, prior to inserting the second base member into the first base member, a filter barrier is dropped into the second base member so that it rests upon the upwardly extending supports in spaced relation relative to the floor. A gasket is then laid atop the filter barrier to cover an outer peripheral flange of the filter barrier. The cup-shaped third base member is then press-fit into the second base member such that the continuous wall of the third base member engages the generally cylindrical inner surface of the second base member in an interference fit, and such that the filter barrier-engaging base presses downwardly upon the gasket. The floor of the third base member provides a needle guard for preventing contact between a needle inserted through the septum into the internal injection chamber, and the filter barrier.

As mentioned above, the third base member includes an upper septum-engaging section which extends upwardly from the continuous wall. As the second base member is then inserted within the first base member, both the septum-engaging section of the third base member, as well as the upwardly extending wall of the second base member compressed the septum peripheral flange against the first base member. This has the effect of sealing the outer peripheral flange of the filter barrier such that the filter barrier divides the internal injection chamber into an upper portion adjacent to the septum, and a lower portion adjacent to the floor. Any fluid injected into the upper portion of the internal injection chamber is required to pass through the filter barrier before being permitted to exit the injection port through the outlet passageway.

Following this assembly, the second base member is heat-staked within the first base member to form a positive mechanical interlock therebetween. The lower reinforced sheet is placed adjacent to the second base member and sealed to the lower flange of the elastomeric outer housing to completely enclose the rigid base members within an elastomeric outer covering.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 3 is an exploded perspective assembly view of the injection port of FIGS. 1 and 2, illustrating the relationship of the primary components thereof, and wherein the upper elastomeric dome is illustrated partly in cross-section.

DETAILED DESCRIPTION OF THE PREFERRED EMBODIMENT

Figure 1:
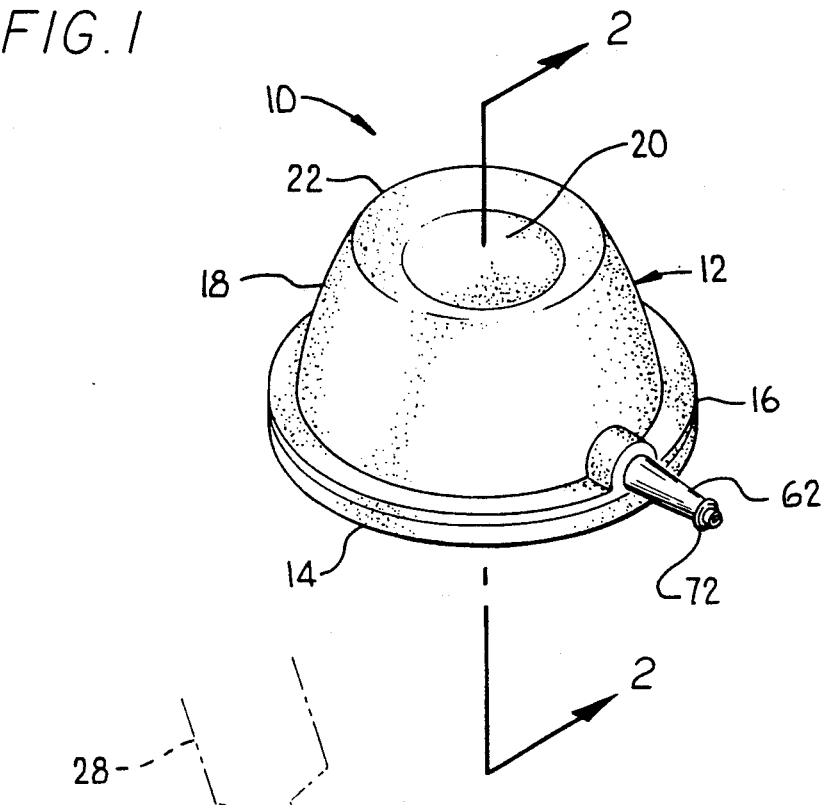
FIG. 1 is a top perspective view of an injection port embodying the invention.

As shown in the drawings for purposes of illustration, the present invention is concerned with an improved subcutaneous injection port, generally designated in the accompanying drawings by the reference number 10. As illustrated best in FIG. 3, the injection port 10 comprises an upper elastomeric dome 12, a lower elastomeric reinforced sheet 14, and a base structure housed within the dome above the reinforced sheet.

The upper dome 12 includes a lower flange 16 which is directly sealed to the reinforced sheet 14 by means of a standard adhesive. Accordingly, the dome 12 and the reinforced sheet 14 present a continuous elastomeric outer housing for the injection port 10, which helps prevent leakage of drugs injected into the housing when the injection port 10 is subcutaneously implanted.

Figure 2:
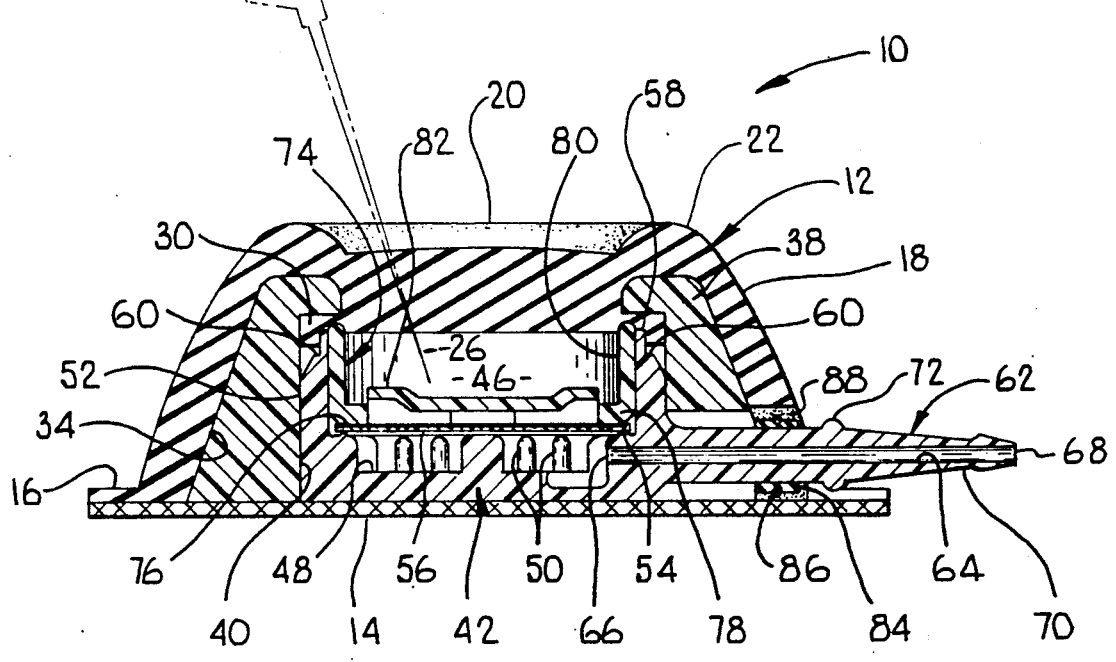
FIG. 2 is an enlarged vertical section taken generally along the line 2—2 of FIG. 1, illustrating the internal components of the injection port in their assembled configuration.

In accordance with the present invention, and as illustrated with respect to a preferred embodiment in FIGS. 1-3, the upper elastomeric dome 12 includes a frusto-conical side wall 18 which extends upwardly from the dome flange 16 to support an integrally formed septum 20 in spaced relation above the lower reinforced sheet 14. The upper end of the side wall 18 surrounding the septum 20 provides means for percutaneously manually locating the septum when the injection port 10 is subcutaneously implanted. More particularly, the side wall 18 includes a ridge 22 which circumscribes an upper exterior surface of the septum 20. The dome 12 is provided with an outlet connector passageway 24 through a lower portion thereof.

The septum 20 comprises a thickened portion of, preferably, a silicone elastomer material having characteristics which permit repeated, intermittent puncture by a needle 26 for injection of drugs from a syringe 28. Such a needle 26 is preferably 20-gauge or smaller. The septum 20 includes a peripheral flange 30 which generally circumscribes a lower end of the septum beneath the ridge portion 22 of the side wall 18. The peripheral flange 30 defines a flange-receiving cavity 32 (FIG. 3) into which a portion of a first base member 34 is positioned.

The first base 34 is preferably formed of a rigid polypropylene material and includes a generally frusto-conical ring 36 configured to contiguously engage and support the interior surface of the dome side wall 18. The first base member 34 further includes a rigid upper flange 38 configured to fit within the flange receiving cavity 32 of the dome 12, and circumscribe the septum 20 to engage the peripheral flange 30. More particularly, the rigid upper flange 38 of the first base member 34 overlies the peripheral flange 30 and provides a rigid barrier between the peripheral flange and the adjacent portions of the dome side wall 18.

Below the rigid upper flange 38 of the first base member 34, the interior of the ring-like side wall 36 forms an inner cylindrical surface 40 which is dimensioned to receive and firmly hold a second base member 42 in an interference fit therein. The first base member 34 includes an outlet connector passageway 44 in the lower end of the ring 36, which is aligned with the outlet connector passageway 24 of the elastomeric dome 12.

The second base member 42 is preferably formed of a rigid polypropylene material and when positioned within the first base member 34, defines, with the septum 20, an internal injection chamber 46. The second base member 42 is generally cup-shaped and includes a floor 48 having a plurality of upwardly extending filter supports 50, and a continuous cylindrical wall 52 which extends upwardly from the floor 48. The wall 52 includes a step 54 spaced the same distance from the floor 48 as the upper ends of the filter supports 50, to provide an outer peripheral supporting surface for a filter barrier 56. An upper septum-engaging section 58 extends upwardly from the upper end of the continuous wall 52 and, in the assembled configuration (FIG. 2), engages the underside of the peripheral flange 30. The upper septum-engaging section 58 meets the continuous wall 52 at a shoulder 60, and is positioned relative to the first base member 34 so as to compress the septum peripheral flange 30 between the section 58 and the rigid upper flange 38. This creates a fluid-tight seal between the base members 34 and 42, on the one hand, and the septum 20 on the other, and further tends to improve the resealing characteristics of the septum.

An outlet is provided in the injection port 10, which extends from the injection chamber 46 exteriorly through the first and second base members 34 and 42, to a point outside of the elastomeric dome 12. More specifically, the outlet includes a rigid outlet connector 62 which, preferably, is integrally formed with the second base member 42. The outlet connector 62 provides a fluid conduit 64 which extends from an inlet port 66 situated on an interior surface of the second base member 42, to an outlet port 68 situated at a distal end of the outlet connector 62. Adjacent to the outlet port 68 is a tapered portion 70 which is configured to receive the end of a catheter or a section of surgical tubing (not shown). Further, a catheter retention knob 72 is formed about the tapered portion 70 to help anchor the catheter or surgical tubing to the outlet connector 62.

The filter barrier 56 extends across the injection chamber 46 and rests atop the filter supports 50 and the wall step 54 provided by the second base member 42. In this manner, the filter barrier separates the injection chamber 46 into an upper portion adjacent to the septum 20, and a lower portion which is in open fluid communication with the fluid conduit 64 through the outlet connector 62. As best shown in FIG. 2, the outer peripheral flange of the filter barrier 56 is positioned directly over the wall step 54, and is secured in place by means of a third base member 74. Preferably, the filter barrier comprises a two-tenths micron filter.

An elastomeric gasket 76 is placed over the outer peripheral flange of the filter barrier 56 and is compressed between the wall step 54 of the second base member 42, and an overlying base 78 of the third base member 74. This effectively provides a means for sealing the outer peripheral flange of the filter barrier 56 adjacent to the second base member 42, to require any fluid injected into the upper portion of the injection chamber 46 to pass through the filter barrier before exiting the injection port 10. The third base member 74 provides a needle guard which prevents contact between the needle 26 inserted through the septum 20 into the injection chamber 46, and the filter barrier 56.

The third base member 74 is preferably formed of a rigid polypropylene material and is generally cup-shaped. The third base member 74 includes the filter barrier-engaging base 78, a continuous cylindrical wall 80 which extends upwardly from the base 78, and a floor 82 spaced from the filter barrier 56 and supported by the base 78. A passageway is provided between the base 78 and the floor 82 to permit fluid flow past the third base member 74 from the upper portion of the injection chamber 46, through the filter barrier 56, and into the lower portion thereof. The continuous wall 80 of the third base member 74 is configured to substantially contiguously engage an inner surface of the wall 52 of the second base member 42 in an interference fit. The upper end of the continuous wall 80 forms an upper septum-engaging section which engages the underside of the septum peripheral flange 30 in much the same manner as the section 58 of the second base member 42. The upper end of the wall 80 is positioned relative to the first base member 34 so as to compress the septum 20 between the upper end of the wall 80 and the rigid upper flange 38.

A barium impregnated silicone seal tube 84 is placed over the outlet connector 62 generally adjacent to the retention knob 72 to be positioned within the outlet connector passageway 24 of the upper dome 12 and the passageway 44 of the first base member 34. The seal tube 84 is secured in place by means of a suture 86, and provides a radiopaque indicator of the orientation of the injection port 10, and specifically the outlet connector 62, when the injection port is subcutaneously implanted. The gap between the seal tube 84 and the dome 12 is filled with a silicone adhesive 88.

The injection port 10 thus described provides a number of manufacturing and functional advantages over similar prior devices. The provision of an elastomeric outer housing comprising the elastomeric dome 12 and the reinforced sheet 14 permits the injection port 10 to present (with the exception of the rigid outlet connector 62), a body of one material for interaction with the patient. It has been found that silicone elastomer materials provide acceptable levels of tissue reaction, and that providing a soft elastomeric outer casing to the injection port 10 enhances the comfort of the injection port to the patient. Further, by completely encasing the base structure within the elastomeric outer housing, the possibility of leakage between the base members and the outer housing is virtually eliminated. A significant advantage of the present design is that assembly of the injection port 10 is greatly facilitated in a manner permitting the peripheral flange 30 of the septum 20 to be captured between separate components of the base structure. By capturing the peripheral flange 30 between the first base member 34 and the second base member 42, a portion of the septum 20 can be compressed to enhance the resealing characteristics of the septum itself, as well as prevent any fluid leakage from the injection chamber 46 past the second base member 42. This ensures that medication injected into the injection chamber 46 flows only through the outlet connector 62 in order to exit the injection port 10, even in the presence of relatively high back-pressure.

An exemplary process for manufacturing the subcutaneously implantable injection port 10, in accordance with the present invention, will now be described. Initially, the first base member 34 is placed within the upper dome 12 such that the rigid upper flange 38 is positioned within the flange receiving cavity 32. When so positioned, the rigid upper flange 38 circumscribes and engages the peripheral flange 30 of the septum 20. Next, the second base member 42 is held upright and the filter barrier 56 is dropped therein so that the outer periphery of the filter barrier 56 rests contiguously over the wall step 54, and interior portions of the filter barrier 56 are supported by the filter supports 50 extending upwardly from the floor 48. The gasket 76 is then placed over the outer peripheral flange of the filter barrier 56 opposite the cylindrical wall 52, and the third base member 74 is press-fit into the second base member 42 such that the base 78 thereof compresses the gasket 76 and the outer peripheral flange of the filter barrier 56 against the wall step 54. As mentioned previously, the third base member 74 is held in place within the second base member 42 by means of an interference fit between the walls 80 and 52.

The second base member 42 is inserted into the first base member 34 to compress the peripheral flange 30 of the septum 20 between the rigid upper flange 38 and the septum-engaging section 58. The second base member 42 is held within the first base member 34 by means of an interference fit between the ring 36 and the cylindrical wall 52. In this manner a fluid-tight internal injection chamber 46 is formed between the septum 20 and the floor 48 of the second base member 42. Further, the third base member 74 is configured such that the upper end of the wall 80 also engages a lower surface of the peripheral flange 30, thereby tending to compress the septum 20 as well as the gasket 76.

The filter barrier 56 divides the internal injection chamber 46 into an upper portion adjacent to the septum 20 and a lower portion adjacent to the floor 48 of the second base member 42. Fluid medication injected into the upper portion of the injection chamber is required to pass through the passageways provided in the third base member 74 and then through the filter barrier 56 before entering the lower portion of the injection chamber 46. The lower portion of the injection chamber comprises a labyrinth passageway in open fluid communication with the inlet port 66 of the fluid conduit 64.

The second base member can then be heat-staked within the first base member to form a positive mechanical interlock therebetween. This is accomplished by locally heat staking the assembly at a temperature of approximately 700° F. The lower reinforced sheet 14 is then adhered to the dome lower flange 16 by means of a silicone adhesive 88, and the gap between the barium impregnated silicone seal tube 84 and the upper dome 12 and underlying portion of the lower reinforced sheet 14 is likewise filled with the silicone adhesive 88.

Although a particular embodiment of the invention has been described in detail for purposes of illustration, various modifications may be made without departing from the spirit and scope of the invention. Accordingly, the invention is not to be limited, except as by the appended claims.

We claim:
1. An injection port, comprising:
   an elastomeric outer housing including an integral elastomeric septum;
   a first base member situated within the outer housing and contiguously engaging a peripheral flange of the septum;
   a second base member situated within the first base member and the outer housing, the second base member contiguously engaging the peripheral flange of the septum opposite the first base member such that the septum is compressed between the first and second base members, wherein the second base member and the septum define an internal chamber;

a filter barrier supported by the second base member, the filter barrier separating the internal chamber into an upper portion adjacent to the septum and a lower portion;

an outlet extending from the lower portion of the internal chamber exteriorly through the outer housing; and means for sealing an outer peripheral flange of the filter barrier adjacent to the second base member, to require any fluid injected into the upper portion of the internal chamber to pass through the filter barrier before passing through the outlet to exit the injection port, wherein the sealing means includes a needle guard for preventing contact between a needle inserted through the septum into the internal chamber, and the filter barrier.

2. An injection port as set forth in claim 1, wherein the sealing means comprises a third base member which is cup-shaped and includes a filter barrier-engaging base, a continuous wall which extends upwardly therefrom, and a floor spaced from the filter barrier and supported by the base, wherein the continuous wall engages an inner surface of the second base member in an interference fit.

3. An injection port as set forth in claim 2, wherein the third base member includes an upper septum-engaging section which extends upwardly from the continuous wall to underlie the peripheral flange of the septum and compress the peripheral flange of the septum between the first base member and the upper septum-engaging section of the third base member.

4. An injection port as set forth in claim 2, wherein the sealing means includes a gasket disposed between the third base member and the outer peripheral flange of the filter barrier, and wherein the filter barrier comprises a two-tenths micron filter.

5. An injection port as set forth in claim 1, wherein the second base member includes a floor having filter supports extending upwardly therefrom for supporting the filter barrier, the upwardly extending floor supports forming a labyrinth passageway in open fluid communication with the outlet.

6. An injection port as set forth in claim 1, wherein the elastomeric outer housing includes an upper dome attached to a lower reinforced sheet, the upper dome including a lower flange sealed to the reinforced sheet, a frusto-conical side wall extending upwardly from the lower flange, and the septum which is integrally formed with the side wall and supported thereby in spaced relation to the lower reinforced sheet.

7. An injection port as set forth in claim 6, wherein the first base member comprises a generally frusto-conical ring configured to engage and support an interior surface of the side wall, and a rigid upper flange which overlies the peripheral flange of the septum to provide a rigid barrier between the peripheral flange of the septum and the adjacent side wall portions, wherein the upper flange circumscribes the septum and engages the peripheral flange of the septum.

8. An injection port as set forth in claim 7, wherein the second base is cup-shaped and includes a floor and a continuous wall which extends upwardly therefrom, wherein the continuous wall projects from the floor to engage an inner surface of the first base member in an interference fit, the wall including an upper septum-engaging section which underlies the peripheral flange of the septum and compresses the peripheral flange of the septum against the upper flange of the first base member.

9. A subcutaneously implantable injection port, comprising:

an elastomeric outer housing including an upper dome attached to a lower reinforced sheet, the upper dome including a lower flange sealed to the reinforced sheet, a frusto-conical side wall extending upwardly from the lower flange, and a septum integrally formed with the side wall and supported thereby in spaced relation to the lower reinforced sheet, the septum including a peripheral flange which extends circumferentially outwardly from the body of the septum toward the side wall;

a rigid first base member enclosed within the elastomeric outer housing, the first base member comprising a generally frusto-conical ring configured to contiguously engage and support an interior surface of the side wall, and a rigid upper flange, wherein the upper flange overlies the peripheral flange of the septum and provides a rigid barrier between the peripheral flange of the septum and the adjacent side wall portions;

a rigid second base member situated within the first base member and the elastomeric outer housing, the second base member being cup-shaped and including a floor and a continuous wall extending upwardly therefrom, the continuous wall engaging an inner surface of the first base member in an interference fit, the second base member defining, with the septum, an internal injection chamber, the second base member further including an upper septum-engaging section which extends upwardly from the continuous wall to underlie the peripheral flange of the septum and compress the peripheral flange of the septum between the upper flange of the first base member and the upper septum-engaging section of the second base member;

a filter barrier supported by the second base member, the filter barrier separating the injection chamber into an upper portion adjacent to the septum and a lower portion;

means for sealing an outer peripheral flange of the filter barrier adjacent to the second base member, to require any fluid injected into the upper portion of the injection chamber to pass through the filter barrier before exiting the injection port, the sealing means including a needle guard for preventing contact between a needle inserted through the septum into the injection chamber, and the filter barrier, the sealing means comprising a third rigid base member, the third base member being cup-shaped and including a filter barrier-engaging base, a continuous wall which extends upwardly therefrom, and a floor spaced from the filter barrier and supported by the base, the continuous wall of the third base member engaging an inner surface of the second base member in an interference fit; and an outlet extending from the lower portion of the injection chamber, exteriorly through the housing, wherein the outlet includes a rigid outlet connector formed integrally with the second base member to provide a fluid conduit from an inlet port on an interior surface of the second base member, to an outlet port situated at an opposite end of the outlet connector.

10. An injection port as set forth in claim 9, wherein the third base member includes a upper septum-engaging section which underlies the peripheral flange of the septum and compresses the peripheral flange of the septum against the upper flange of the first base member.

11. An injection port as set forth in claim 9, wherein the sealing means includes a gasket disposed between the third base member and the outer peripheral flange of the filter barrier, and wherein the filter barrier comprises a two-tenths micron filter.

12. An injection port as set forth in claim 9, wherein the floor of the second base member includes filter supports extending upwardly therefrom for supporting the filter barrier, the upwardly extending floor supports forming a labyrinth passageway in open fluid communication with the outlet.

13. An injection port, comprising:
an elastomeric outer housing including an integral elastomeric septum;
a first base member situated within the outer housing and contiguously engaging a peripheral flange of the septum;
a second base member situated within the first base member and the outer housing, the second base member contiguously engaging the peripheral flange of the septum opposite the first base member such that the septum is compressed between the first and second base members, wherein the second base member and the septum define an internal chamber;
a filter barrier supported by the second base member, the filter barrier separating the internal chamber into an upper portion adjacent o the septum and a lower portion; and
an outlet extending from the lower portion of the internal chamber exteriorly through the outer housing;
wherein the second base member includes a floor having filter supports extending upwardly therefrom for supporting the filter barrier, the upwardly extending floor supports forming a labyrinth passageway in open fluid communication with the outlet.

14. An injection port as set forth in claim 13, including means for sealing an outer peripheral flange of the filter barrier adjacent to the second base member, to require any fluid injected into the upper portion of the internal chamber to pass through the filter barrier before passing through the outlet to exit the injection port.

15. An injection port as set forth in claim 13, wherein the elastomeric outer housing includes an upper dome attached to a lower reinforced sheet, the upper dome including a lower flange sealed to the reinforced sheet, a frusto-conical side wall extending upwardly from the lower flange, and the septum which is integrally formed with the side wall and supported thereby in spaced relation to the lower reinforced sheet.

16. An injection port as set forth in claim 15, wherein the first base member comprises a generally frusto-conical ring configured to engage and support an interior surface of the side wall, and a rigid upper flange which overlies the peripheral flange of the septum to provide a rigid barrier between the peripheral flange of the septum and the adjacent side wall portions, wherein the upper flange circumscribes the septum and engages the peripheral flange of the septum.

17. An injection port as set forth in claim 16, wherein the second base is cup-shaped and includes a floor and a continuous wall which extends upwardly therefrom, wherein the continuous wall projects from the floor to engage an inner surface of the first base member in an interference fit, the wall including an upper septum-engaging section which underlies the peripheral flange of the septum and compresses the peripheral flange of the septum against the upper flange of the first base member.

* * * * *

UNITED STATES PATENT AND TRADEMARK OFFICE
CERTIFICATE OF CORRECTION

PATENT NO.  : 5,137,529

DATED       : August 11, 1992

INVENTOR(S) : David A. Watson, Mark J. Licata, Alfons Heindl and Edward C. Leicht It is certified that error appears in the above-identified patent and that said Letters Patent is hereby corrected as shown below:

In column 11, line 36, delete "o" after the word "adjacent" and insert therefor --to--.

Signed and Sealed this

Fourteenth Day of September, 1993

Attest:

BRUCE LEHMAN

Attesting Officer            Commissioner of Patents and Trademarks